United States Patent [19]

Bonaldi

[11] Patent Number: 5,349,074
[45] Date of Patent: Sep. 20, 1994

[54] PROCESS FOR PHARMACEUTICAL GRADE HIGH PURITY HYODEOXYCHOLIC ACID PREPARATION

[75] Inventor: Antonio Bonaldi, Chiuduno, Italy

[73] Assignee: Erregierre Industria Chimica S.p.A., S. Paola D'Argon, Italy

[21] Appl. No.: 10,149

[22] Filed: Jan. 28, 1993

[30] Foreign Application Priority Data

Mar. 11, 1992 [IT] Italy .............................. MI92 A 0560

[51] Int. Cl.⁵ ..................... C07C 35/44; C07C 29/92
[52] U.S. Cl. .................................................. 552/551
[58] Field of Search ........................................ 552/551

[56] References Cited

U.S. PATENT DOCUMENTS

| | | | |
|---|---|---|---|
| 2,745,849 | 5/1956 | Fogle | 552/551 |
| 4,163,744 | 8/1979 | Kaiser | 552/551 X |
| 4,186,143 | 1/1980 | Ziegler et al. | 552/551 |
| 4,217,279 | 8/1980 | Kaiser | 552/551 X |

*Primary Examiner*—Johann Richter
*Assistant Examiner*—Michael B. Hydorn
*Attorney, Agent, or Firm*—Oliff & Berridge

[57] ABSTRACT

Process for pharmaceutical grade high purity hyodeoxycholic acid preparation starting from swine bile, consisting in the treatment of swine bile with sodium hydroxide, isolation of hyodeoxycholic, chenodeoxycholic and hyocholic acids by precipiation of their zinc salts and subsequent selective precipitation of the hyodeoxycholic acid magnesium salt, from which the acid is freed by acidification and then crystallized.

14 Claims, No Drawings

PROCESS FOR PHARMACEUTICAL GRADE HIGH PURITY HYODEOXYCHOLIC ACID PREPARATION

PRIOR ART

Various hyodeoxycholic acid preparation processes starting from swine bile are known from literature, e.g. as described in U.S. Pat. Nos. 2,758,120 and 3,006,927. All such methods are adversely affected by their being extremely laborious, hence industrially burdensome; moreover, they are scarcely effective insofar as product purity is concerned.

SUMMARY

We have now found a new process based on simple, economic and high yield steps allowing to obtain high purity hyodeoxycholic acid starting from swine bile.

The process is characterized by the fact that:

a) swine bile is made react with an NaOH aqueous solution;

b) the reaction mixture is added with an organic solvent plus water and treated with a mineral acid to liberate biliary acids and remove the other bile components;

c) the biliary acids solution is treated with an ammonium zincate aqueous solution to precipitate the zinc salts of the same biliary acids;

d) the zinc salts of the biliary acids are treated, in an organic solvent plus water environment, with a mineral acid to liberate biliary acids;

e) the biliary acid solution is treated with a magnesium salt to selectively precipitate the magnesium salt present in the hyodeoxycholic acid and remove the other biliary acids;

f) the hyodeoxycholic acid magnesium salt is treated, in an organic solvent plus water environment, with a mineral acid for the purpose of liberating the hyodeoxycholic acid and removing magnesium as a salt of said mineral acid;

g) hyodeoxycholic acid is recovered at high purity, by crystallization.

DETAILED DESCRIPTION OF THE INVENTION

The features of the process for the preparation of hyodeoxycholic acid by the present invention will be better described in detail hereinafter.

The process raw material is swine bile with a water content ranging from 10 to 80% and containing taurine-conjugated hyodeoxycholic, chenodeoxycholic and hyocholic acids. Said acids are also referred to simply as biliary acids.

Bile is treated to reflux with a 10 to 50% sodium hydroxide solution, for 20–30 hours.

The mixture resulting from this treatment is taken up with water and added with an organic solvent selected from the group consisting of $C_1$ to $C_4$ alcohol acetate, propionate, and butyrate. Preferably ethyl acetate is used, mixed with water. The mixture obtained is added with a mineral salt selected among sulphuric, hydrochloric and phosphoric acids, in such a quantity as to secure a 3 to 5 pH.

The organic phase of the mixture contains biliary acids, while the aqueous phase contains all the other bile components. Thus the aqueous phase is separated and removed, while the organic phase is Further treated For the obtainment of hyodeoxycholic acid. Then, the organic phase is treated with an ammonium zincate aqueous solution at a concentration ranging from 30 to 200 g/l, the ammonium zincate/initial bile weight ratio ranging From 0.02 to 0.1.

The treatment is carried out at a temperature From 0° C. to 60° C. and brings about the precipitation of the zinc salts of the three biliary acids, namely of hyodeoxycholic acid, chenodeoxycholic acid, and hyocholic acid. The suspension is allowed to cool to a temperature ranging From 0° C. to 10° C. and is filtered; the solid product is washed with an ethyl acetate-water mixture. This operation is meant to remove the impurities contained in the biliary acids.

The solid product consisting, as said above, of the three biliary acids zinc salts mixture is resuspended in a mixture Formed by water and one of the aforesaid organic solvents, then it is heated to a temperature ranging from 30° C. to 80° C., and acidified with a mineral acid to a pH ranging from 0 to 2.5. The aqueous phase, which contains zinc sulphate, is eliminated, while the organic phase, which contains free biliary acids, is added with water and then with ammonia until reaching a pH ranging from 8 to 9. The thus obtained mixture is added with a magnesium salt solution, such a salt being chosen among chloride, sulphate and acetate, with a magnesium concentration ranging from 20 to 60 g/l, the ammonium zincate/initial bile weight ratio ranging from 0.004 to 0.02. This operation is conducted at a temperature ranging from 0° C. to 60° C. and leads to the iodeoxycholic acid magnesium salt selective precipitation, whilst chenodeoxycholic and hyocholic acid magnesium salts remain in the solution.

The suspension is allowed to cool, if necessary, to a temperature ranging from 0° C. to 20° C. ; then, it is filtered for the removal of the solution and the recovery of the solid consisting of hyodeoxycholic acid magnesium salt. The solid is washed with an ethyl acetate aqueous solution; the suspension thus obtained is heated to a temperature ranging from 40° C. to 60° C. and acidified with a mineral acid to a pH between 1 and 3 to liberate hyodeoxycholic acid.

The aqueous phase containing the magnesium salt of said mineral acid is separated and eliminated. The organic phase, which contains hyodeoxycholic acid, undergoes purification by water washing and activated carbon filtering; then, it is vacuum concentrated to the removal of approx. half the solvent volume. Finally, by cooling to about 0° C. , hyodeoxycholic acid crystallizes and is recovered as pure product as a result of standard operations, such as filtering, washing, and drying.

The hyodeoxycholic acid obtained via the invention process exhibits a high purity level, which makes it suitable for pharmaceutical use.

Moreover, the various process stages are based on simple high efficiency operations.

The following examples are conveyed by way of indication, not of limitation.

EXAMPLE 1

2.5 kg concentrated swine bile with a 36% water content was treated with 1.5 kg 30% sodium hydroxide and refluxed for 20 hours. Then, the mixture was taken up with 1 l water and 2 l ethyl acetate. Further to the addition of 35% sulphuric acid, the pH was brought to approx. 4.

The aqueous phase, separated at 50° C., was eliminated, while the organic phase was treated with an ammonium zincate aqueous solution at a concentration of 70 g/l, the ammonium zincate/initial swine bile weight ratio being equal to 0.06.

The zinc salts of iodeoxycholic, chenodeoxycholic and hyocholic acids precipitated.

The mixture was allowed to cool to 0° C.; the product was filtered and washed with an ethyl acetate aqueous solution.

The moist product was suspended in 1000 ml water and 1000 ml ethyl acetate, heated to 50° C., and acidified with sulphuric acid approx. to pH 2.

The aqueous phase containing zinc sulphate was separated, prior to elimination.

The organic phase was treated with 1000 ml water.

The pH was corrected in the 8 to 9 range by NH$_3$ addition; then, a magnesium sulphate aqueous solution at a concentration of 170 g/1 was added, the magnesium sulphate/initial bile weight ratio being 0.04.

The precipitation of the hyodeoxycholic acid magnesium salt occurred soon.

After cooling to 0° C., the product was filtered and washed with an ethyl acetate aqueous solution. The moist product was eventually suspended in 1000 ml deionized water and 1000 ml ethyl acetate, heated to 50° C., then the mixture was acidified with sulphuric acid.

The aqueous phase containing magnesium sulphate was separated. The organic phase containing hyodeoxycholic acid was water-washed twice, then filtered with decolourizing carbon and vacuum concentrated to half its volume.

The residual solution was allowed to cool to 0° C., the hyodeoxycholic acid was filtered and then washed thoroughly with ethyl acetate at first and then with water.

Drying at 70° C. yielded 120 g pure product with the following characteristics:

Grade: 100.0% (by titration with NaOH 0.1 N);
$[\alpha]^{20}_D = +8.2°$;
m.p. = 196°–200° C.;
HPLC purity >99.0% (presence of traces of chenodeoxycholic and hyocholic acids).

EXAMPLE 2

Example 1 was repeated using ethyl isopropyl acetate as solvent and magnesium chloride as magnesium salt. The final product purity was slightly below that resulting in Example 1, mainly owing to the presence of hyocholic acid.

EXAMPLE 3

Example 1 was repeated using ethyl isobutyl acetate as solvent and magnesium acetate as magnesium salt. The final product purity was slightly below that resulting in Example 1, mainly owing to the presence of chenodeoxycholic and hyocholic acids.

I claim:

1. Process for the preparation of high purity hyodeoxycholic acid starting from swine bile, wherein:
   a) swine bile is made to react with an NaOH aqueous solution;
   b) the reaction mixture is added with an organic solvent plus water and treated with a mineral acid to liberate biliary acids and remove the other bile components;
   c) the biliary acids solution is treated with an ammonium zincate aqueous solution to precipitate the zinc salts of the same biliary acids;
   d) the zinc salts of the biliary acids are treated, in an organic solvent plus water environment, with a mineral acid to liberate the biliary acids;
   e) the biliary acid solution is treated with a magnesium salt to selectively precipitate the magnesium salt of the hyodeoxycholic acid and remove the other biliary acids;
   f) the hyodeoxycholic acid magnesium salt is treated, in an organic solvent plus water environment, with a mineral acid for the purpose of liberating the hyodeoxycholic acid and removing magnesium as a salt of said mineral acid;
   g) hyodeoxycholic acid is recovered at high purity, by crystallization.

2. Process as per claim 1, wherein the organic solvent is selected from the group consisting of the acetate, propionate and butyrate of an alcohol having one to four carbon atoms.

3. Process as per claim 1, wherein the organic solvent is ethyl acetate.

4. Process as per claim 1, wherein the mineral acid is selected from the group consisting of sulphuric acid, phosphoric acid and hydrochloric acid.

5. Process as per claim 1, wherein the treatment with mineral acid as per point b) is conducted until pH is 3 to 5.

6. Process as per claim 1, wherein the treatment with the ammonium zincate aqueous solution is conducted at a temperature ranging from 0° C. to 60° C.

7. Process as per claim 1, wherein the treatment with mineral acid as per point d) is conducted until pH is 0 to 2.5.

8. Process as per claim 1, wherein hyodeoxycholic acid magnesium salt precipitation takes place at a pH value from 8 to 9 and at a temperature ranging from 0° C. to 60° C.

9. Process as per claim 1, wherein hyodeoxycholic acid magnesium salt precipitation is brought about by a magnesium salt selected from the group consisting of magnesium sulphate, magnesium, chloride and magnesium acetate.

10. Process as per claim 1, wherein the treatment with mineral acid as per point f) is conducted until pH is 1 to 3.

11. Process as per claim 1, wherein crystallization takes place in an organic solvent selected from the group consisting of the acetate, propionate and butyrate of an alcohol having one to four carbon atoms.

12. Process as per claim 1, wherein crystallization occurs upon cooling to 0° C.

13. Process as per claim 1, wherein the treatment with ammonium zincate aqueous solution takes place with an ammonium zincate/initial bile weight ratio ranging from 0.02 to 0.1.

14. Process as per claim 1, wherein the treatment with magnesium salt takes place with a magnesium/initial bile weight ratio ranging from 0.004 to 0.02.

* * * * *